(12) United States Patent
Sarraf et al.

(10) Patent No.: US 11,571,142 B2
(45) Date of Patent: Feb. 7, 2023

(54) FALL DETECTION AND IDENTIFICATION BY USING DATA FROM HUMAN CONDITION SAFETY TAGS

(71) Applicant: American International Group, Inc., New York, NY (US)

(72) Inventors: Mohsen Sarraf, New York, NY (US); Sergey Vikhlyantsev, New York, NY (US); Jennifer Martinez, New York, NY (US)

(73) Assignee: AMERICAN INTERNATIONAL GROUP, INC., New York, NY (US)

( * ) Notice: Subject to any disclaimer, the term of this patent is extended or adjusted under 35 U.S.C. 154(b) by 233 days.

(21) Appl. No.: 16/515,999

(22) Filed: Jul. 18, 2019

(65) Prior Publication Data
US 2020/0022623 A1 Jan. 23, 2020

Related U.S. Application Data (60) Provisional application No. 62/700,027, filed on Jul. 18, 2018.

(51) Int. Cl.
*A61B 5/11* (2006.01)
*A61B 5/00* (2006.01)
*G16H 50/30* (2018.01)

(52) U.S. Cl.
CPC .......... *A61B 5/1117* (2013.01); *A61B 5/0022* (2013.01); *A61B 5/7246* (2013.01); *A61B 5/7282* (2013.01); *G16H 50/30* (2018.01); *A61B 2562/0219* (2013.01)

(58) Field of Classification Search
CPC .......... A61B 5/1117; A61B 2562/0219; A61B 5/0022; A61B 5/002; A61B 5/1123
USPC ....................................................... 600/595
See application file for complete search history.

(56) References Cited

U.S. PATENT DOCUMENTS

| 7,395,709 | B2 * | 7/2008 | Noda ....................... G01P 15/18 360/75 |
| 9,638,711 | B2 * | 5/2017 | Barfield ................... G01P 15/00 |
| 2005/0096569 | A1 * | 5/2005 | Sato ........................ A61B 5/1118 600/595 |
| 2006/0247104 | A1 * | 11/2006 | Grabiner ............ A63B 22/0235 482/54 |
| 2007/0250286 | A1 | 10/2007 | Duncan et al. |

(Continued)

OTHER PUBLICATIONS

Casilari, E., Santoyo-Ramón, J. A., & Cano-García, J. M. (2016). Analysis of a smartphone-based architecture with multiple mobility sensors for fall detection. PLoS One, 11(12), e0168069. (Year: 2016).*

*Primary Examiner* — Daniel L Cerioni
*Assistant Examiner* — Jonathan E. Cooper
(74) *Attorney, Agent, or Firm* — Snell & Wilmer L.L.P.

(57) ABSTRACT

A fall detection and identification system includes a tag worn by a user and a server. The tag collects acceleration data from one or more sensors embedded within the tag and transmits the data to the server. The server receives the data from the tag and performs an analysis on the data to detect and identify a fall. The analysis includes determining a change in acceleration of the user over the time window based on the acceleration data; comparing the change in acceleration of the user against one or more thresholds; and determining a status of the user based on the comparison of the change in acceleration of the user against the one or more thresholds.

12 Claims, 7 Drawing Sheets

(56) References Cited

U.S. PATENT DOCUMENTS

| | | | |
|---|---|---|---|
| 2009/0292227 A1* | 11/2009 | Scholten | A61B 5/0031 600/595 |
| 2011/0179850 A1 | 7/2011 | Klinnert et al. | |
| 2014/0276240 A1 | 9/2014 | Stein et al. | |
| 2015/0164377 A1* | 6/2015 | Nathan | A61B 5/6802 600/595 |
| 2016/0029954 A1* | 2/2016 | Sato | A61B 5/6804 702/141 |
| 2016/0089080 A1* | 3/2016 | Li | A61B 5/681 702/141 |
| 2016/0113551 A1* | 4/2016 | Annegarn | A61B 5/7275 600/595 |
| 2017/0281054 A1* | 10/2017 | Stever | A61B 5/113 |
| 2017/0312515 A1 | 11/2017 | Ferree et al. | |
| 2018/0070889 A1* | 3/2018 | Lee | A61B 5/1122 |
| 2018/0263534 A1* | 9/2018 | Lee | G16H 40/67 |
| 2018/0338708 A1* | 11/2018 | Chan | A61B 5/1118 |
| 2019/0103007 A1* | 4/2019 | Tan | G08B 21/0446 |

\* cited by examiner

Find Confidence Interval

| Confidence Level: | ●95% ○99% |
|---|---|
| Sample Size: | 34 |
| Population: | 100000000 |
| Percentage: | 97.059 |

[Calculate] [Clear]

Confidence Interval: 5.68

FIG. 7A

Find Confidence Interval

| Confidence Level: | ●95% ○99% |
|---|---|
| Sample Size: | 34 |
| Population: | 100000000 |
| Percentage: | 2.941 |

[Calculate] [Clear]

Confidence Interval: 5.68

FIG. 7B

Find Confidence Interval

| Confidence Level: | ●95% ○99% |
|---|---|
| Sample Size: | 15 |
| Population: | 100000000 |
| Percentage: | 6.667 |

[Calculate] [Clear]

Confidence Interval: 12.62

FIG. 7C

Find Confidence Interval

| Confidence Level: | ○95% ●99% |
|---|---|
| Sample Size: | 34 |
| Population: | 100000000 |
| Percentage: | 97.059 |

[Calculate] [Clear]

Confidence Interval: 7.48

FIG. 7D

Find Confidence Interval

| Confidence Level: | ○95% ●99% |
|---|---|
| Sample Size: | 34 |
| Population: | 100000000 |
| Percentage: | 2.941 |

[Calculate] [Clear]

Confidence Interval: 7.48

FIG. 7E

Find Confidence Interval

| Confidence Level: | ○95% ●99% |
|---|---|
| Sample Size: | 15 |
| Population: | 100000000 |
| Percentage: | 6.667 |

[Calculate] [Clear]

Confidence Interval: 16.62

FIG. 7F

FALL DETECTION AND IDENTIFICATION BY USING DATA FROM HUMAN CONDITION SAFETY TAGS

CROSS-REFERENCE TO RELATED APPLICATIONS

This patent application claims the benefit of U.S. Provisional Patent Application No. 62/700,027, filed on Jul. 18, 2018, which is incorporated by reference.

BACKGROUND

Injuries can occur in work environments where an individual's work duties require that they be present in a potentially hazardous area or perform a potentially hazardous activity. For instance, at a construction site, manufacturing facility, warehouse or any other such work environment, people regularly handle heavy equipment or packages, and/or move about in potentially hazardous spaces or perform regular job tasks in a potentially dangerous non-ergonomic manner. Over time, some individuals working at these potentially hazardous locations or performing these potentially hazardous activities may be injured due to a fall or repeatedly performing a task in a non-ergonomic manner. Additionally, when an individual performs a task in a non-ergonomic manner, safety personnel would need to witness the activity in order to instruct the individual to perform the action in a more ergonomic fashion, and even if safety personnel were able to intervene, they have no way to monitor the individual going forward to make sure the activity is no longer being performed in the non-ergonomic manner.

BRIEF SUMMARY

In one embodiment, the disclosure provides a fall detection and identification system. The system includes a tag configured to be worn by a user. The tag includes a network interface and an acceleration sensor configured to collect acceleration data of the user over time. The system further includes a server communicatively coupled to the tag and configured to receive the acceleration data of the user from the tag and analyze the acceleration data over a time window to determine a status of the user. The analysis performed by the server utilizing the acceleration data from the tag includes: determining a change in acceleration of the user over the time window; comparing the change in acceleration of the user against one or more thresholds; and determining a status of the user based on the comparison of the change in acceleration of the user against the one or more thresholds.

In another embodiment, the disclosure provides a server for performing a fall detection and identification analysis based on acceleration data of a user collected by a user wearable tag. The server includes a processor and a memory storing instructions that when executed by the processor configure the server to perform steps including: receiving the acceleration data from the user wearable tag during a time window; determining a change in acceleration of the user over the time window based on the acceleration data; comparing the change in acceleration of the user against one or more thresholds; and determining a status of the user based on the comparison of the change in acceleration of the user against the one or more thresholds.

In yet another embodiment, the disclosure provides a method of fall detection and identification based on acceleration data of a user collected by a user wearable tag. The method includes: receiving the acceleration data from the user wearable tag during a time window; determining a change in acceleration of the user over the time window based on the acceleration data; comparing the change in acceleration of the user against one or more thresholds; and determining a status of the user based on the comparison of the change in acceleration of the user against the one or more thresholds.

DETAILED DESCRIPTION

An embodiment of the disclosure provides a fall detection and identification system. The system includes a tag worn by a user and a server configured to communicate with the tag. The tag is configured to collect data from one or more sensors embedded in the tag and transmit the data from the one or more sensors to the server. The server is configured to receive the data from the tag and perform an analysis on the data to determine whether the user has fallen or fainted. Further and alternative aspects and features of the disclosed principles will be appreciated from the following detailed description and the accompanying drawings. As will be appreciated, the principles relating to detecting the occurrence of a human operator suffering a fall disclosed herein are capable of being carried out in other and different embodiments, and capable of being modified in various respects. Accordingly, it is to be understood that the following detailed description is exemplary and explanatory only.

Injuries occur in work environments such as construction sites, manufacturing facilities, warehouses or any other such work environments where people regularly handle heavy equipment or packages, and/or move about in potentially hazardous spaces or perform regular job tasks in a potentially dangerous non-ergonomic manner. Over time, some individuals working at these potentially hazardous locations or performing these potentially hazardous activities may be injured due to a fall or repeatedly performing a task in a non-ergonomic manner. Additionally, when an individual performs a task in a non-ergonomic manner, safety personnel would need to witness the activity in order to instruct the individual to perform the action in a more ergonomic fashion, and, even if safety personnel did witness the activity, they have no way to monitor the individual going forward to make sure the activity is no longer being performed in the non-ergonomic manner.

Figure 1:
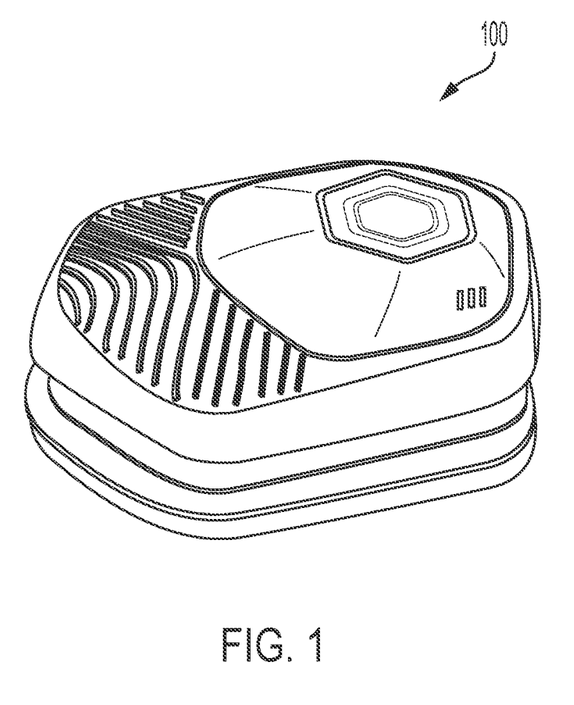
FIG. 1 provides a view of a tag, in accordance with an embodiment of this disclosure.

Accordingly, acquiring instantaneous knowledge of a person's activities and potential injury status would be beneficial for responding to an injury in a timely fashion and providing knowledge regarding the injury to individuals responding to the injury. Embodiments of the disclosure provide a user wearable tag that incorporates one or more sensors that when worn by the user will measure data and report that data to a server over a wireless link. FIG. 1 illustrates tag 100, in accordance with an embodiment of the disclosure. The tag 100 is a light weight tag that may be attached to a user's clothing while the user is going about daily work activities. In certain embodiments, a user wears only one tag 100 located either in a safety jacket, on a helmet, or any other convenient location, generally on the upper portion of the body, such as, for example, at the "T" of the spine on the upper back just below the neck.

Figure 2:
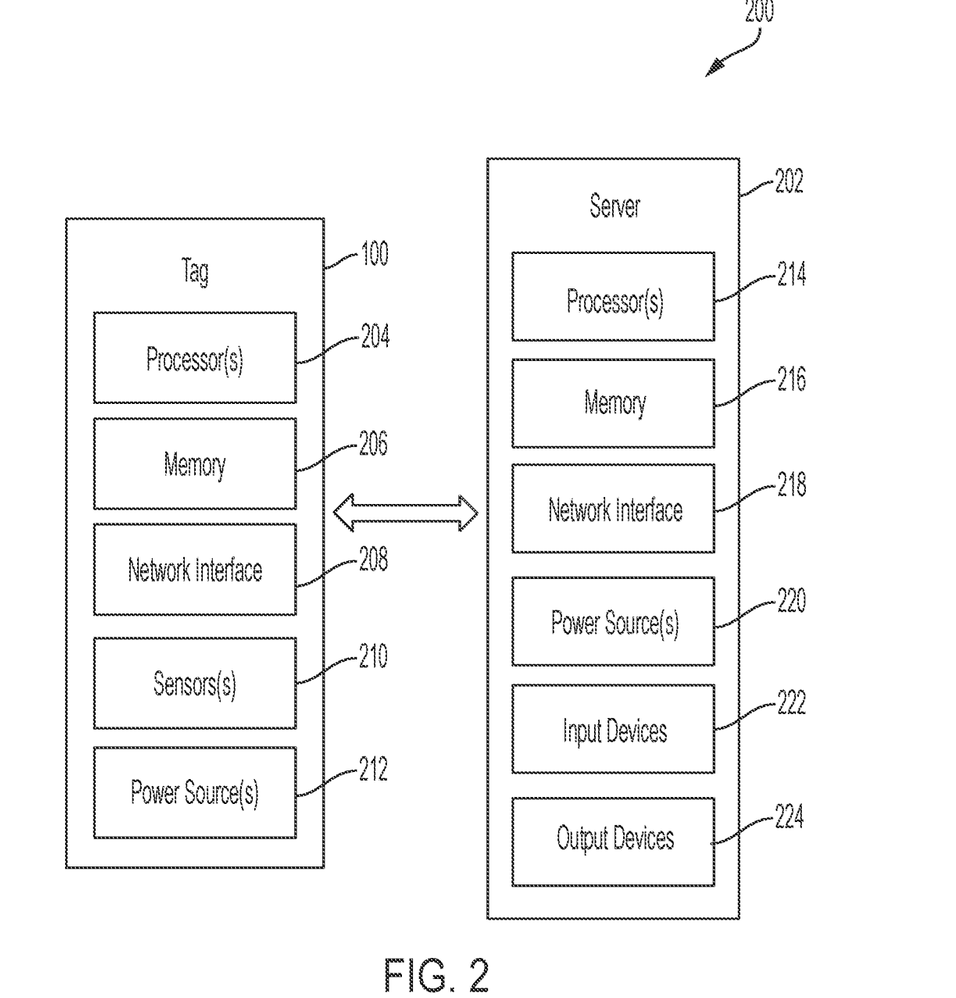
FIG. 2 illustrates a block diagram of a system for fall detection and identification, in accordance with an embodiment of this disclosure.

FIG. 2 illustrates a block diagram of a system 200 for fall detection and identification. System 200 incorporates the tag 100 and a server 202, wherein the tag 100 communicates with the server 202. As illustrated, tag 100 includes one or more processor(s) 204, a memory 206, a network interface 208, one or more sensors 210, and a power source 212. Although not explicitly shown in FIG. 2, each component provided is interconnected physically, communicatively, and/or operatively for inter-component communications in order to realize functionality ascribed to the tag 100.

The processor 204 is configured to implement functions and/or process instructions for execution within tag 100. For example, the processor 204 executes instructions stored in memory 206. The memory 206, which may be a non-transient, computer-readable storage medium, is configured to store information within the tag 100 during operation. In some embodiments, the memory 206 includes a temporary memory that does not retain information stored when the tag 100 is turned off. Examples of such temporary memory include volatile memories such as random access memories (RAM), dynamic random access memories (DRAM), and static random access memories (SRAM).

The network interface 208 is used to communicate with external devices and/or servers, such as the server 202. The tag 100 may comprise multiple network interfaces 208 to facilitate communication via multiple types of networks. The network interface 208 can comprise one or more radio frequency transceivers or any other type of device that can send and receive information. Non-limiting examples of network interface 208 include radios compatible with several Wi-Fi standards, 3G, 4G, Long-Term Evolution (LTE), Bluetooth®, etc.

The power source(s) 212 provides power to the tag 100. In certain embodiments, the power source 212 comprises a battery. In embodiments where the power supply 212 is a battery, that battery may be either rechargeable or non-rechargeable. Where the battery is rechargeable, the tag 100 may include a port for receiving power from a power adaptor plugged into a suitable electricity source, such as, a typical wall outlet for example.

As mentioned above, the tag 100 further includes one or more sensors 210 that are utilized to collect data, such as a location of the tag, an acceleration of the tag in one or more directions, and/or any other such sensor data that may be collected based on a type of sensor embedded in the tag 100. For instance, the one or more sensors 210 may include an accelerometer measuring acceleration data in three mutually perpendicular axes (x, y, and z directions) to determine instantaneous movement of the user in three dimensional space. The sensors 210 may also incorporate a Global Positioning System (GPS) device or other such position determining sensor or technique so the tag 100 can provide its geographic location to the server 202.

In embodiments, the server 202 includes one or more processor(s) 214, a memory 216, a network interface 218, the power source(s) 220, the input devices 222 and the output devices 224. Although not explicitly shown in FIG. 2, each component provided is interconnected physically, communicatively, and/or operatively for inter-component communications in order to realize functionality ascribed to the server 200.

The processor 214 is configured to implement functions and/or process instructions for execution within the server 202. For example, the processor 214 executes instructions stored in the memory 216. The memory 216, which can be any suitable non-transient, computer-readable storage medium, is configured to store information within the server 202 during operation. In some embodiments, the memory 216 includes a temporary memory that does not retain information stored when the server 202 is turned off. Examples of such temporary memory include volatile memories such as random access memories (RAM), dynamic random access memories (DRAM), and static random access memories (SRAM). The memory 216 can also maintain program instructions for execution by the processor 214.

The network interfaces 218 can be used to communicate with external devices such as the tag 100. The server 202 may comprise multiple network interfaces 218 to facilitate communication via multiple types of networks. The network interfaces 218 can comprise suitable network interface cards, such as Ethernet cards, optical transceivers, radio frequency transceivers, or any other type of device that can send and receive information. Non-limiting examples of network interfaces 218 include radios compatible with several Wi-Fi standards, 3G, 4G, Long-Term Evolution (LTE), Bluetooth®, etc.

The power source(s) 220 provides power to the server 202. For example, the server 202 may include a regulator for regulating power from the power grid when the server 202 is plugged into a wall outlet.

In some embodiments, the server 202 is equipped with one or more input devices 222. The input devices 222 are configured to receive input from a user of the server 202 or the environment where the server 202 resides. In certain instances, the input devices 222 include devices that provide interaction with the environment through tactile, audio, and/or video feedback. These may include a presence-sensitive screen or a touch-sensitive screen, a mouse, a keyboard, a video camera, microphone, a voice responsive system, or any other type of input device.

In some embodiments, the server 202 can also be equipped with one or more output devices 224. The output device 224 can be configured to provide output to a user of the server 202 using tactile, audio, and/or video information. Examples of a suitable output device 224 include a display (cathode ray tube (CRT) display, liquid crystal display (LCD) display, LCD/light emitting diode (LED) display, organic LED display, etc.), a sound card, a video graphics adapter card, speakers, magnetic, or any other type of device that may generate an output intelligible to the user of the server 202.

The server 202 is configured to perform an algorithmic analysis of data collected by the one or more sensors 210 of the tag 100. In this manner, the server 202 analyzes the data to determine whether it satisfies a predetermined condition to trigger an indication that assistance or intervention for a user of tag 100. For instance, the tag 100 can provide data that when analyzed by the server 202 indicates that the user has suffered a fall. In this instance, the server 202 will identify that the user has suffered the fall and alert assistance personnel to a potential injury to the user. Additionally, the server 202 may collect and store the acceleration data over time. By analyzing an extended period of this data, the server 202 will be able to determine that the user is performing activities in a potentially harmful manner, such as bending over or lifting an object in a less than ideal manner.

In certain embodiments, the above determination of a user falling may be made by the server 202 applying an algorithm utilizing the data collected from the tag 100. In a particular embodiment, the one or more sensors 210 of the tag 100 include an accelerometer that collects acceleration data in three mutually perpendicular axes (x, y and z directions). If a user of the tag 100 falls or trips, a higher than usual acceleration is produced over a short period of time at the moment of impact. Therefore, the algorithm performed by the server 202 can be configured to detect such higher than usual acceleration in a relatively short period of time.

In certain embodiments, in order to render the algorithm calibration-free, the three accelerations in the x, y and z directions reported by the tag 100 are combined into a single value representing a total acceleration change. In this manner, orientation of the accelerometer within the tag 100 can be disregarded, thereby reducing processing time and overhead at the server 202. Typically, for combining the accelerations from each dimension (x, y and z) into a total acceleration, a square root of the sum total of each acceleration component squared is determined, as shown in Equation (1) below.

$$A_{total}((A_X)^2+(A_Y)^2+(A_Z)^2)^{1/2} \quad (1)$$

In Equation (1), $A_X$, $A_Y$ and $A_Z$ are the total, x, y and z components of the acceleration respectively and represent three time series signals reported by the accelerometer.

As evident in Equation (1), three square and addition operations per sample time are performed. In certain embodiments, because the system is interested in much higher than usual changes in acceleration regardless of which direction it came from and also because it is interested in large changes and not necessarily their absolute actual resulting value, an estimate of the total acceleration can be utilized. Equation (2) below provides an exemplary equation to determine this estimation of the total acceleration.

$$A_{totalEst}=|A_X|+|A_Y|+|A_Z| \quad (2)$$

$A_{totalEst}$ is an estimate of the total resulting acceleration and may be made by the server 202 with less calculation complexity and without regard to a direction of acceleration.

The calculation of $A_{totalEst}$ in Equation (2) is performed per sample time and observed over a sliding window time of $T_{win}$ sample times. The window can be established to be sliding in that, for each new set of samples arriving from the accelerometer, an old set of samples are discarded. In this fashion, the window is sliding along with time over the arriving acceleration samples. During this window period, the minimum and maximum values produced by Equation (2) are collected and a difference between those values is calculated. This difference is termed the acceleration swing over the window time. This acceleration swing can be compared against a threshold. If the swing is above the threshold, the system can be configured to indicate that a fall has taken place during this time period.

Figure 3:
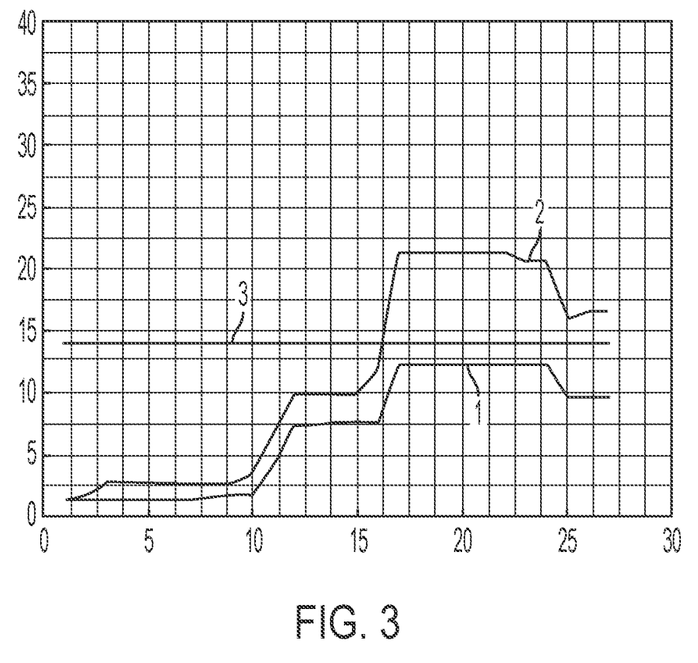
FIG. 3 provides a plot of acceleration swing over time, in accordance with an embodiment of this disclosure.

FIG. 3 illustrates example acceleration swings over time produced by Equations (1) and (2). The window size in FIG. 3 is 10 samples. The vertical axis represents the acceleration swing in m/s², and the horizontal axis represents time. The acceleration swing based on Equation (1) is shown by curve 1, and the acceleration swing based on Equation (2) is shown by curve 2. Additionally, a threshold of 14 m/s² is also shown as line 3. The 14 m/s² threshold is provided for illustration purposes, as the threshold could be set to a different value, such as 19 or 20 m/s².

As shown in FIG. 3, curve 1 reaches a lower peak compared to curve 2, meaning that in setting thresholds, acceleration swing data from Equation (1) may be more susceptible to false alarms than acceleration swing data from Equation (2). This is because when using Equation (1), the threshold would need to be set lower to avoid mistaking bends with falls, as they also provide acceleration peaks similar to falls when using Equation (1). However, using Equation (2) reduces such chances for a false fall indication because the threshold may be set higher, which helps to provide a greater distinction between a fall and a bend.

Because there are other actions the user can take that might result in excess acceleration, such as bending (either at waist or at knees), the threshold can be set in a range that is high enough in order to avoid false positives (i.e., false alarm) and low enough in order to avoid false negatives (i.e., miss). Empirical data can be used to establish such threshold ranges, which allows for setting thresholds that provide high probability of detection with relatively very low probabilities of false alarm and miss.

In certain embodiments, two thresholds can be utilized. In these embodiments, various types of falls can be distinguished due to different acceleration data profiles. For instance, a fall occurring because of a trip can be distinguished from a fall occurring because the user fainted. A fall based on a trip is indicated by a sudden and short in time jolt in acceleration followed by acceleration data indicating a fall has occurred in general. A fall based on a faint has a different acceleration profile because no initial jolt is found in the data. As such, a faint can be determined by the indication of a fall without the initial jolt in acceleration. The two thresholds can be termed Threshold-Faint (THF) and Threshold-Trip (THT). As an aside, distinguishing between a trip and a faint utilizing a single threshold is possible in situations with less of a difference in acceleration swing between a trip and a faint.

Figure 4:
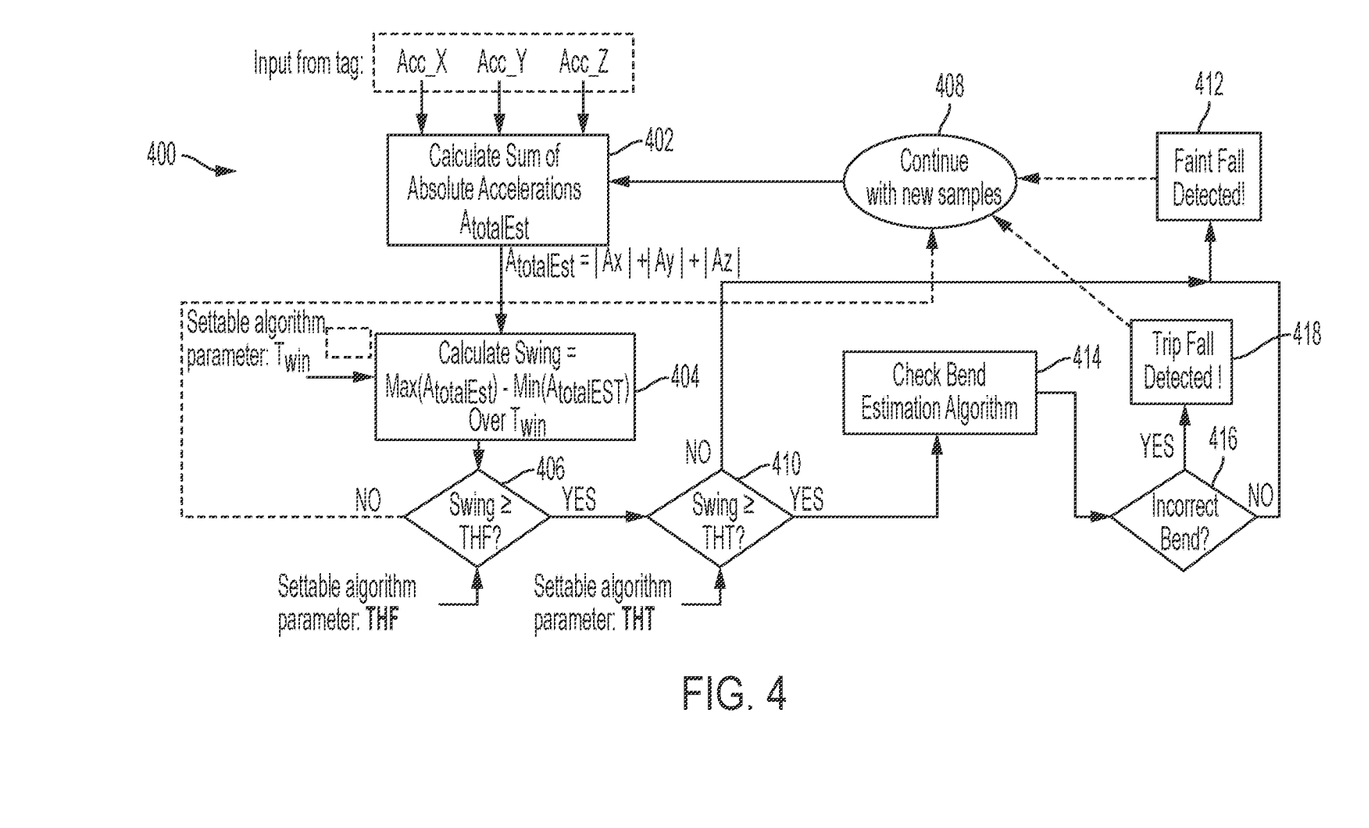
FIG. 4 provides a flow chart illustrating an algorithm for fall detection, in accordance with an embodiment of this disclosure.

FIG. 4 illustrates an algorithm 400 for detecting a fall that uses two thresholds, THF and THT. The server can be used to execute the algorithm 400 continuously based on acceleration data collected from the tag 100 (see FIG. 1), and fall determinations are made by analyzing the acceleration data collected over a particular time window. At step 402, the server makes a calculation to determine a total estimated acceleration using Equation (2). At step 404, the server calculates an acceleration swing over the time window by determining a difference between maximum and minimum total estimated acceleration data points collected during the time window.

At step 406, the server compares the acceleration swing against THF to determine whether the user has fainted. If the acceleration swing is less than THF, the algorithm 400 proceeds to continue analyzing new samples at step 408. If the acceleration swing is greater than or equal to THF, the algorithm 400 proceeds to compare the acceleration swing against THT at step 410. If the acceleration swing is less than THT, then a faint is detected at step 412. Whereas, if the acceleration swing is greater than or equal to THT, the algorithm 400 proceeds to check the acceleration swing utilizing a Bend Estimation Algorithm at step 414 to determine whether the user performed an incorrect bend (at the waist) or a correct bend (at the knees). An incorrect bend applies excessively high torque to a user's lower back, and a correct bend applies a low overall torque to the lower back. The output of the Bend Estimation Algorithm check from step 414 is analyzed at step 416 to determine if it was an incorrect bend. If the output does not indicate an incorrect bend, the algorithm 400 indicates a faint at step 412. If the output does indicate an incorrect bend, the algorithm 400 indicates a trip at step 418 and proceeds to continue analyzing new samples at step 408.

Figure 5:
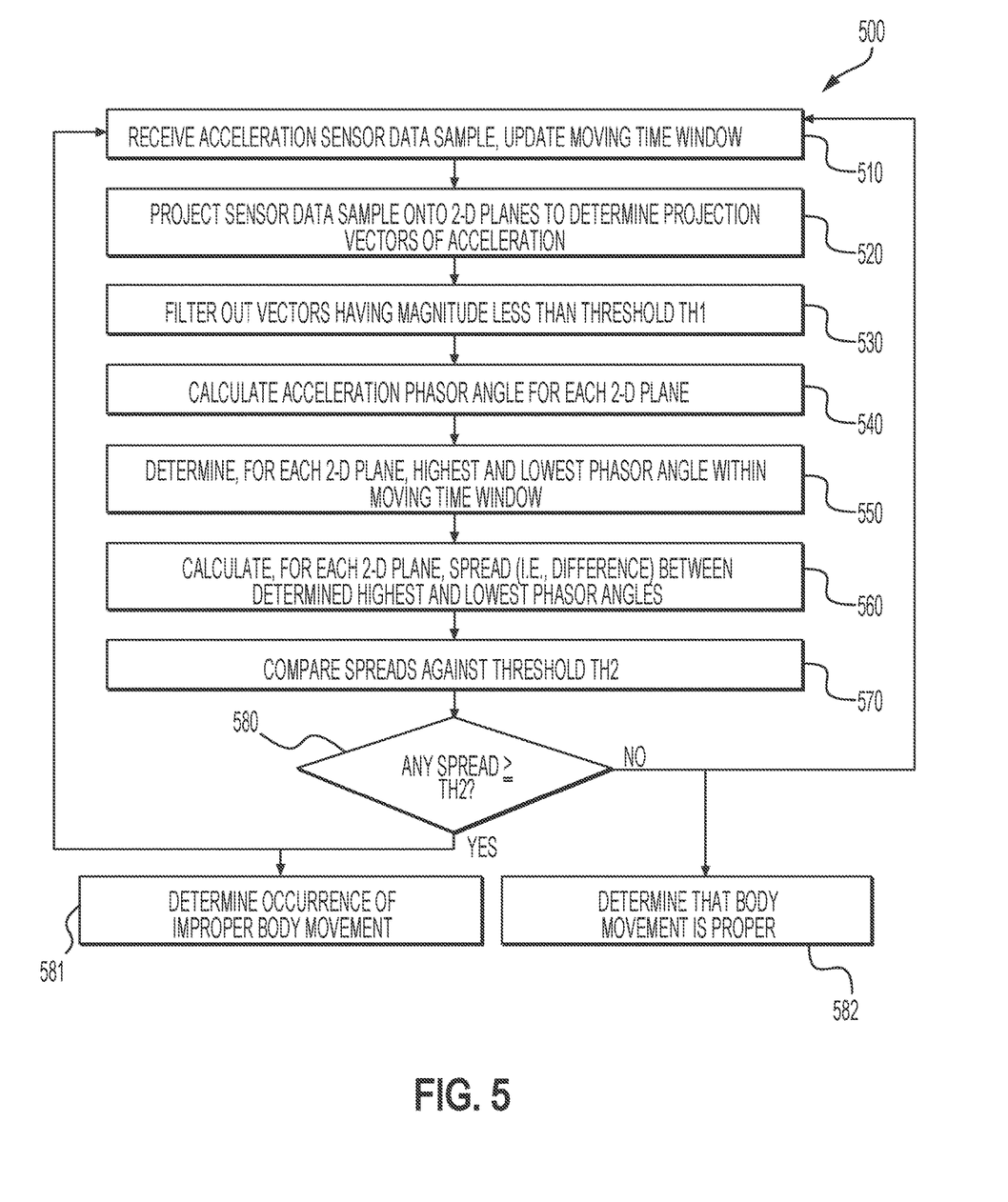
FIG. 5 illustrates a Bend Estimation Algorithm, in accordance with an embodiment of this disclosure.

FIG. 5 illustrates an exemplary Bend Estimation Algorithm 500 that may be used at step 414 of FIG. 4, in accordance with a particular embodiment of this disclosure. In certain embodiments, the Bend Estimation Algorithm 500 is performed by the processor 214 of the server 202 (see FIG. 2) as described below.

In step 510, the processor 214 (see FIG. 2) receives acceleration data samples collected from the acceleration sensor 210 of the tag 100 and transmitted through its network interface 208. The processor 214 updates the moving time window, discarding the oldest data sample within the moving time window. In certain embodiments, the time window used for the Bend Estimation Algorithm 500 is the same as the time window used for algorithm 400 of FIG. 4.

In step 520, the processor 214 projects the received acceleration data samples onto multiple 2-D planes (e.g., an X-Y plane, an X-Z plane, and a Y-Z plane) and determines projection vectors of proper acceleration for each 2-D plane. Each projection vector corresponds to a direction and magnitude of acceleration in the respective 2-D plane.

In step 530, the processor 214 filters out projection vectors that have a magnitude less than a threshold TH1. This filtering process removes vectors corresponding to small amounts of acceleration, which would not constitute major body movements.

In step 540, the processor 214 calculates, for each 2-D plane, an acceleration phasor angle based on the projection vector by using an inverse tangent calculation or by using a look-up table. Equation (3) below is an example of the inverse tangent calculation for the X-Y plane.

$$\theta_{XY} = \tan^{-1}\frac{\text{(acceleration magnitude along the } X \text{ direction)}}{\text{(acceleration magnitude along the } Y \text{ direction)}} \quad (3)$$

Also, in step 540, the moving time window is updated to include the calculated phasor angles.

In step 550, the processor 214 determines, for each 2-D plane, the highest and the lowest phasor angle for that 2-D plane within the moving time window. In step 560, the processor 214 calculates, for each 2-D plane, the angle spread (i.e., angle difference) between the highest and the lowest phasor angle for that 2-D plane within the moving time window.

In step 570, the processor 214 compares each of the angle spreads (e.g., three angle spreads for the three 2-D planes) against a threshold TH2. In step 580, the processor 214 determines whether any of the angle spreads equals or exceeds the threshold TH2. If any one of the angle spreads equals or exceeds the threshold TH2, the processor 214 identifies that an improper body movement has occurred within the moving time window, in step 581. Otherwise, the processor 214 identifies that no improper body movement has occurred, in step 582. After either determination, the operation awaits the next acceleration data sample, and returns to step 510.

Based on experimental data, Table 1 below provides probabilities of detection, miss and false alarms as a function of comparing an acceleration swing against the faint threshold THF, in accordance with a particular embodiment of the disclosure. In Table 1, the probability of detection is the number of times a fall is detected out of the total test runs; however, the probability of false alarm is calculated based on the THF threshold being crossed due to not a fall but a bend (another body motion that can produce wide swings in the reported accelerations). The probability of a miss is simply derived by determining the probability of detection subtracted from one.

Table 1 shows a threshold setting of 16 m/s² will provide the best performance when all performance metrics are considered. As shown, the results of Table 1 are based on experimental data performed utilizing 34 test points.

TABLE 1

Performance of faint fall versus Threshold (THF)

| Threshold (m/s²) | P(Detection) | P(Miss) | P(False Alarm) |
|---|---|---|---|
| 14 | 33/34 ≈ 0.971 | 1/34 ≈ 0.029 | 4/15 ≈ 0.267 |
| 15 | 33/34 ≈ 0.971 | 1/34 ≈ 0.029 | 2/15 ≈ 0.133 |
| 16 | 33/34 ≈ 0.971 | 1/34 ≈ 0.029 | 1/15 ≈ 0.067 |
| 17 | 30/34 ≈ 0.882 | 4/34 ≈ 0.118 | 1/15 ≈ 0.067 |

Figure 6:
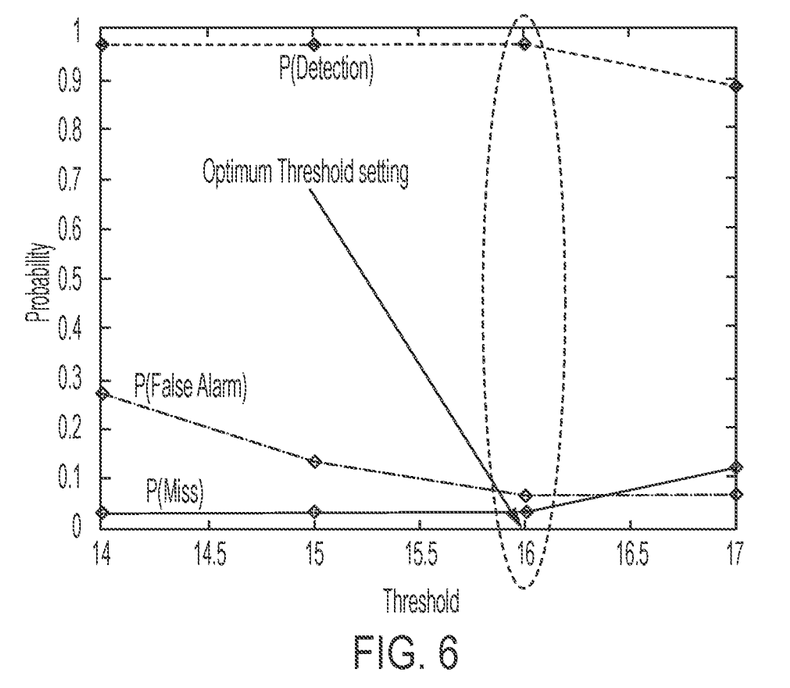
FIG. 6 provides a plot of faint/fall performance results, in accordance with an embodiment of this disclosure.

The results of Table 1 are graphically illustrated in FIG. 6. As shown, an optimum threshold setting is determined by finding the acceleration swing threshold that maximizes the probability of detection and minimizes the probability of miss and the probability of false alarm.

Figure 7A:
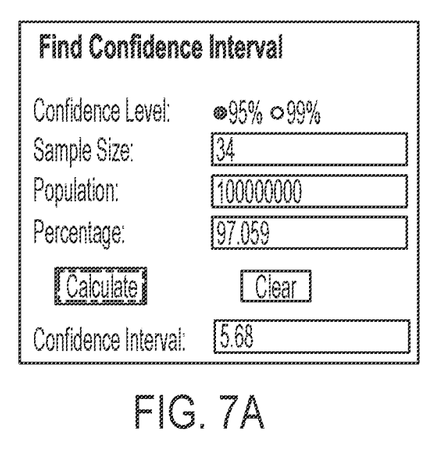
FIGS. 7a-7f provides confidence intervals for faint/fall performance results testing, in accordance with an embodiment of this disclosure.
Figure 7B:
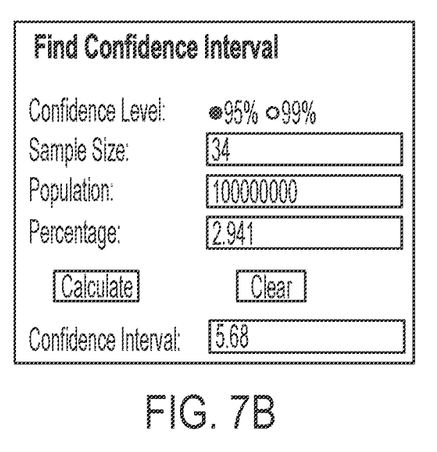
Figure 7C:
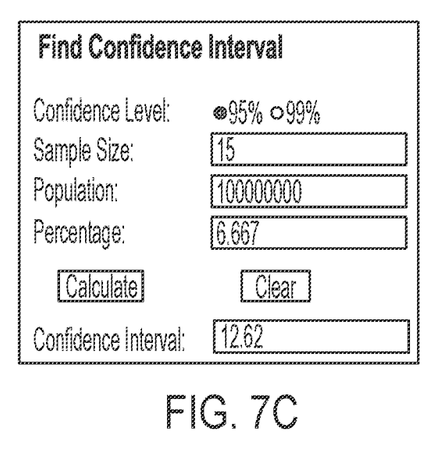
Figure 7D:
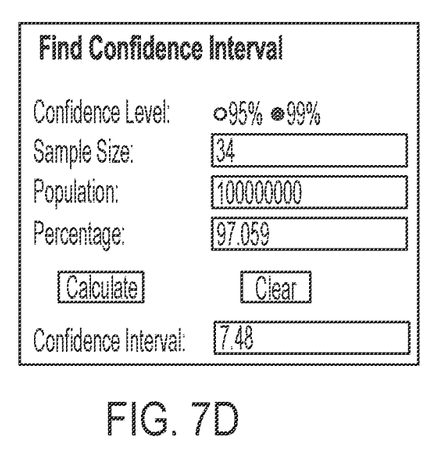
Figure 7E:
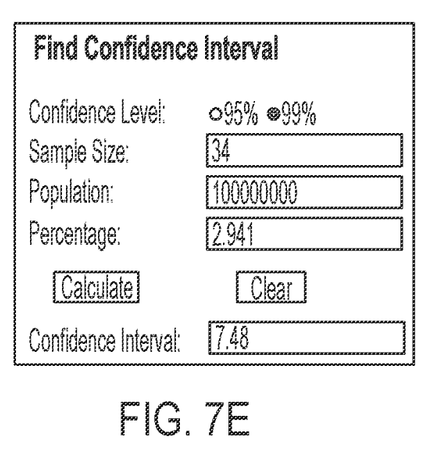
Figure 7F:
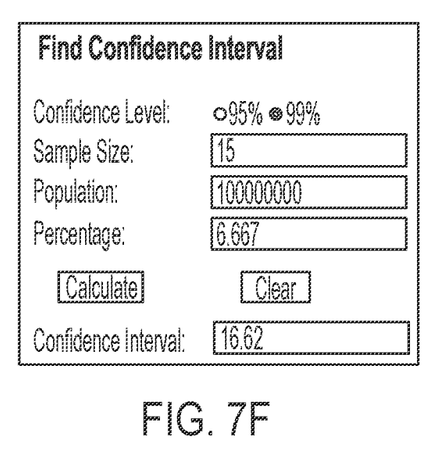

FIGS. 7a-7f provide confidence intervals for the performance result provided above. FIGS. 7a and 7d, respectively, provide 95% and 99% confidence intervals for P(Detection). FIGS. 7b and 7e, respectively, provide 95% and 99% confidence intervals for P(Miss). FIGS. 7c and 7f, respectively, provide 95% and 99% confidence intervals for P(False Alarm).

As an example of data represented in each figure, FIG. 7a indicates that a probability of detection in a population of 100,000,000 based on 34 samples result is at least 0.91379 (97.059%-5.68%) with a 95% confidence level. The data in FIGS. 7b-7f are determined based on the same population and samples.

Similar to the data in Table 1 used to determine an optimal faint threshold THF, an optimal trip threshold THT can also be determined experimentally. A trip threshold THT of 19 m/s² or 20 m/s² is optimal and results in a probability of detection of 1 (i.e., 100% detection, resulting in probability of miss being zero) and a probability of false alarm of 0 (i.e., there were no bends confused with trip falls). Similar confidence interval analyses shows that the confidence interval for a population of 100000000 use cases is tighter than 4.26% and 5.6% for 95% and 99% confidence intervals respectively. In other words, for example, with 95% confidence the probability of detection will be higher than 0.9574.

The above disclosure is provided in relation to injuries that occur at a work site. However, the disclosure is equally applicable to injuries occurring in various non-work locations as well, such as at a gymnasium, playground, park, or other facility as will be appreciated by one skilled in the art. Therefore, the embodiments of the disclosure discussed above are not limited to monitoring an employee's activities at a work site but rather to preventing injuries and improving response times to an injury regardless of the location where the injury may occur.

Embodiments of the disclosed principles may be implemented in a computer program for running on a computer system, at least including code portions for performing steps of a method according to the invention when run on a programmable apparatus, such as a computer system or enabling a programmable apparatus to perform functions of a device or system according to the invention.

A computer program is a list of instructions such as a particular application program and/or an operating system. The computer program may for instance include one or more of: a subroutine, a function, a procedure, an object method, an object implementation, an executable application, an applet, a servlet, a source code, an object code, a shared library/dynamic load library and/or other sequence of instructions designed for execution on a computer system.

The computer program may be stored internally on computer readable storage medium or transmitted to the computer system via a computer readable transmission medium. All or some of the computer program may be provided on transitory or non-transitory computer readable media permanently, removably or remotely coupled to an information processing system. The computer readable media may include, for example and without limitation, any number of the following: magnetic storage media including disk and tape storage media; optical storage media such as compact disk media (e.g., CD-ROM, CD-R, etc.) and digital video disk storage media; non-volatile memory storage media including semiconductor-based memory units such as FLASH memory, EEPROM, EPROM, ROM; ferromagnetic digital memories; MRAM; volatile storage media including registers, buffers or caches, main memory, RAM, etc.; and data transmission media including computer networks, point-to-point telecommunication equipment, and carrier wave transmission media, just to name a few.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A fall detection and identification system comprising:
    a tag configured to be worn by a user, wherein the tag comprises a network interface and an acceleration sensor configured to collect acceleration data of the user over time; and
    a server communicatively coupled to the tag,
    wherein the server is configured to receive the acceleration data of the user from the tag, and
    wherein the server includes a processor that is configured to analyze the acceleration data over a moving time window to determine a status of the user by:
    estimating, by the processor, a total acceleration over a moving time window and based on a sum of absolute values of acceleration in the x-direction, acceleration in the y-direction and acceleration in the z-direction;
    determining, by the processor, a maximum of the total acceleration over the moving time window;
    determining, by the processor, a minimum of the total acceleration over the moving time window;
    determining, by the processor, an acceleration swing based on a difference between the maximum of the total acceleration over the moving time window and the minimum of the total acceleration over the moving time window;
    establishing, by the processor, a trip threshold, in response to an initial jolt in acceleration;
    establishing, by the processor, a faint threshold, in response to a lack of the initial jolt in acceleration;
    comparing, by the processor, the acceleration swing against the faint threshold;
    determining, by the processor, that a faint occurred, in response to the acceleration swing being greater than or equal to the faint threshold and less than the trip threshold;
    determining, by the processor, that a possible trip occurred, in response to the acceleration swing being greater than or equal to the trip threshold;
    determining, by the processor, that the possible trip is the faint, in response to the bend estimation algorithm indicating a lack of an incorrect bend;
    determining, by the processor, that the possible trip is a trip, in response to the bend estimation algorithm indicating an incorrect bend,
    wherein the bend estimation algorithm indicates the incorrect bend by:
        projecting, by the processor, the acceleration data onto a plurality of 2-D planes to determine projection vectors of acceleration for each 2-D plane of the plurality of 2-D planes, wherein each projection vector corresponds to a direction and magnitude of acceleration in each respective 2-D plane;

filtering, by the processor, the projection vectors having a magnitude less than a vector threshold;

determining, by the processor, an acceleration phasor angle for each of the 2-D planes based on the projection vector by using an inverse tangent calculation;

updating, by the processor, the moving time window to include the acceleration phasor angle;

determining, by the processor, a highest phasor angle and a lowest phasor angle within the moving time window, for each of the 2-D planes;

determining, by the processor, a phasor angle difference between the highest phasor angle and the lowest phasor angle, for each of the 2-D planes;

determining, by the processor, an occurrence of an improper body movement of the user within the moving time window comprising the user performing the incorrect bend at the waist, in response to the phasor angle difference for any of the three phasor angle differences for the three 2-D planes, being equal to or greater than a phasor angle threshold.

2. The system of claim 1, wherein the acceleration sensor of the tag collects the acceleration data of the user in three spatial directions.

3. A server comprising:
a processor; and
a memory storing instructions that when executed by the processor configure the server to perform steps comprising:
receiving, by the processor, acceleration data from a user wearable tag worn by a user during a moving time window;
estimating, by the processor, a total acceleration over a moving time window and based on a sum of absolute values of acceleration in the x-direction, acceleration in the y-direction and acceleration in the z-direction;
determining, by the processor, a maximum of the total acceleration over the moving time window;
determining, by the processor, a minimum of the total acceleration over the moving time window;
determining, by the processor, an acceleration swing based on a difference between the maximum of the total acceleration over the moving time window and the minimum of the total acceleration over the moving time window;
establishing, by the processor, a trip threshold, in response to an initial jolt in acceleration;
establishing, by the processor, a faint threshold, in response to a lack of the initial jolt in acceleration;
comparing, by the processor, the acceleration swing against the faint threshold;
determining, by the processor, that a faint occurred, in response to the acceleration swing being greater than or equal to the faint threshold and less than the trip threshold;
determining, by the processor, that a possible trip occurred, in response to the acceleration swing being greater than or equal to the trip threshold;
determining, by the processor, that the possible trip is the faint, in response to the bend estimation algorithm indicating a lack of an incorrect bend;
determining, by the processor, that the possible trip is a trip, in response to the bend estimation algorithm indicating an incorrect bend, wherein the bend estimation algorithm indicates the incorrect bend by:
projecting, by the processor, the acceleration data onto a plurality of 2-D planes to determine projection vectors of acceleration for each 2-D plane of the plurality of 2-D planes, wherein each projection vector corresponds to a direction and magnitude of acceleration in each respective 2-D plane;
filtering, by the processor, the projection vectors having a magnitude less than a vector threshold;
determining, by the processor, an acceleration phasor angle for each of the 2-D planes based on the projection vector by using an inverse tangent calculation;
updating, by the processor, the moving time window to include the acceleration phasor angle;
determining, by the processor, a highest phasor angle and a lowest phasor angle within the moving time window, for each of the 2-D planes;
determining, by the processor, a phasor angle difference between the highest phasor angle and the lowest phasor angle, for each of the 2-D planes;
determining, by the processor, an occurrence of an improper body movement of the user within the moving time window comprising the user performing the incorrect bend at the waist, in response to the phasor angle difference for any of the three phasor angle differences for the three 2-D planes, being equal to or greater than a phasor angle threshold.

4. The system of claim 1, further comprising a position determining sensor configured to provide a geographic location of the tag to the server.

5. The system of claim 1, wherein the server is configured to alert assistance personnel to a potential injury of the user based on the status of the user.

6. The system of claim 1, wherein the moving time window is a sliding window such that a new set of the acceleration data is used and an old set of the acceleration data is discarded.

7. The system of claim 1, wherein the 2-D planes include an X-Y plane, an X-Z plane and a Y-Z plane.

8. The system of claim 1, wherein the vector threshold corresponds to a small amount of acceleration that represents small body movements.

9. A method comprising:
receiving, by a processor, acceleration data from a user wearable tag worn by a user during a moving time window;
estimating, by the processor, a total acceleration over a moving time window and based on a sum of absolute values of acceleration in the x-direction, acceleration in the y-direction and acceleration in the z-direction;
determining, by the processor, a maximum of the total acceleration over the moving time window;
determining, by the processor, a minimum of the total acceleration over the moving time window;
determining, by the processor, an acceleration swing based on a difference between the maximum of the total acceleration over the moving time window and the minimum of the total acceleration over the moving time window;
establishing, by the processor, a trip threshold, in response to an initial jolt in acceleration;
establishing, by the processor, a faint threshold, in response to a lack of the initial jolt in acceleration;
comparing, by the processor, the acceleration swing against the faint threshold;

determining, by the processor, that a faint occurred, in response to the acceleration swing being greater than or equal to the faint threshold and less than the trip threshold;

determining, by the processor, that a possible trip occurred, in response to the acceleration swing being greater than or equal to the trip threshold;

determining, by the processor, that the possible trip is the faint, in response to the bend estimation algorithm indicating a lack of an incorrect bend;

determining, by the processor, that the possible trip is a trip, in response to the bend estimation algorithm indicating an incorrect bend, wherein the bend estimation algorithm indicates the incorrect bend by:

projecting, by the processor, the acceleration data onto a plurality of 2-D planes to determine projection vectors of acceleration for each 2-D plane of the plurality of 2-D planes, wherein each projection vector corresponds to a direction and magnitude of acceleration in each respective 2-D plane;

filtering, by the processor, the projection vectors having a magnitude less than a vector threshold;

determining, by the processor, an acceleration phasor angle for each of the 2-D planes based on the projection vector by using an inverse tangent calculation;

updating, by the processor, the moving time window to include the acceleration phasor angle;

determining, by the processor, a highest phasor angle and a lowest phasor angle within the moving time window, for each of the 2-D planes;

determining, by the processor, a phasor angle difference between the highest phasor angle and the lowest phasor angle, for each of the 2-D planes;

determining, by the processor, an occurrence of an improper body movement of the user within the moving time window comprising the user performing the incorrect bend at the waist, in response to the phasor angle difference for any of the three phasor angle differences for the three 2-D planes, being equal to or greater than a phasor angle threshold.

10. The system of claim 1, wherein the determining the acceleration phasor angle includes using a look-up table.

11. The system of claim 1, wherein the determining the acceleration phasor angle includes updating the moving time window.

12. The system of claim 1, further comprising determining that the user has not fallen, in response to the phasor angle difference being lower than the phasor angle threshold.

* * * * *